United States Patent [19]

Kydd

[11] Patent Number: 4,491,955
[45] Date of Patent: Jan. 1, 1985

[54] FLUID FLOW AND ASH CONCENTRATION METER SYSTEM USING MOSSBAUER EFFECT

[75] Inventor: Paul H. Kydd, Lawrenceville, N.J.

[73] Assignee: HRI, Inc., Gibbsboro, N.J.

[21] Appl. No.: 393,941

[22] Filed: Jun. 30, 1982

[51] Int. Cl.³ .............................................. G01T 1/16
[52] U.S. Cl. ........................................ 378/3; 378/210
[58] Field of Search ............................................ 378/3

[56] References Cited

U.S. PATENT DOCUMENTS

| | | | |
|---|---|---|---|
| 3,146,624 | 9/1964 | Talbot | 378/3 |
| 3,452,200 | 6/1969 | Matthews | 378/3 |
| 3,872,333 | 3/1975 | Imbut | 378/3 |
| 4,352,288 | 10/1982 | Paap | 378/47 |

Primary Examiner—Craig E. Church
Attorney, Agent, or Firm—Fred A. Wilson

[57] ABSTRACT

A meter system and method for measuring the velocity and metal concentration of a fluid containing a gamma ray absorbing metal isotope flowing in a pipe. The meter system comprises a radioactive source of gamma rays which is oscillated in a direction angled to the fluid flow, an accelerometer device incorporated with the gamma ray source, gamma ray detector means located adjacent a pipe portion for detecting the presence of a metal isotope in the flowing fluid, and an electrical circuit and meter means arranged for measuring and displaying the velocity of the oscillating source of gamma rays when the metal isotope in the flowing fluid is absorbing gamma radiation. If desired, the concentration of gamma ray absorbing isotopes such as iron compounds contained in the flowing fluid can be monitored by a counter means to measure the metal concentration of the fluid, or ash concentration of a flowing coal-derived liquid.

15 Claims, 1 Drawing Figure

FLUID FLOW AND ASH CONCENTRATION METER SYSTEM USING MOSSBAUER EFFECT

BACKGROUND OF INVENTION

This invention pertains to a meter system for determining fluid flow velocity and metal concentration for fluids containing a metal isotope using the Mossbauer effect. It pertains particularly to a meter system and method for determining flowing velocity and ash concentration of coal-derived liquids flowing through a pipe.

There is a great need for instruments to continuously measure flow rate and ash content of coal-derived liquids in coal liquefaction processes. It is known that there are radioactive isotopes of cobalt, iron and other elements which emit gamma rays of such precise wavelength that it is possible to measure Doppler shifts at velocities in the centimeter/second range. A general description of the Mossbauer effect and spectroscopy techniques is provided in "An Introduction to Mossbauer Spectroscopy" by L. May, pages 1-44, Plenum Press, 1971. Use of Mossbauer spectroscopy techniques to analyze pyritic content of coal and coal-related samples such as ash residue materials is discussed in FUEL, 1978, Vol 57, p. 592-603. Further information regarding use of Mossbauer spectroscopy analysis is provided in "Analytical Methods for Coal and Coal Products", Vol. III, Chapter 50, Academic Press, 1979, and in "Mossbauer Spectroscopy and Its Chemical Applications", J. G. Stevens, and G. K. Shenoy, Advances in Chemistry Series 194, Chapters 7-9, American Chemical Society, 1981.

It has now been unexpectedly found that such metal isotopes can be used to measure flow velocities and also to measure ash content of coal-derived liquids flowing through a pipe. A meter system making use of the Mossbauer effect can provide a useful means for remotely measuring both flow rates and ash concentrations simultaneously for such coal-derived liquids, and the system also has general utility in the hydrocarbon processing industry.

SUMMARY OF INVENTION

The present invention discloses a metering system for determining the velocity of a flowing fluid containing a gamma ray absorbing metal isotope in a pipe, and a method for using the metering system. The metering system comprises a radioactive source of gamma rays positioned adjacent and in alignment with a pipe portion through which a fluid containing a gamma ray absorbing metal isotope is flowing. The gamma ray source is shielded and oriented toward the pipe portion and is oscillated at a maximum linear forward velocity exceeding that of the flowing fluid. The gamma ray source has an accelerometer device incorporated therein for measuring the linear velocity of the oscillated source at any instant. A gamma ray counter or detector means for detecting gamma ray absorption by particles in the flowing fluid is positioned on a side of the pipe portion opposite the gamma ray source, and is effectively shielded from the gamma ray emitting radioactive source by suitable shielding means. An electrical circuit connects the gamma ray source accelerometer means to the gamma ray absorption detector, for monitoring the velocity of said oscillating gamma ray source and the absorption of gamma rays by flowing metal particles in the pipe and thereby measuring the velocity of the flowing fluid in the pipe portion. The velocity of the flowing fluid is conveniently displayed by a suitable meter.

In operation, when the forward velocity of oscillating source of gamma rays substantially matches that of the flowing fluid containing a gamma ray absorbing metal isotope, the gamma rays will be absorbed by metal particles in the following fluid and such absorption is monitored by the gamma ray counter means. The signal from the gamma ray detector accelerometer is used to latch a counter meter which monitors the forward velocity of the radiation source. Thus, whenever the velocity of the oscillating source matches that of the flowing fluid, the velocity of the oscillating source is indicated by the meter, thereby measuring the velocity of the fluid flowing in the pipe. Metals contained in the flowing fluid and for which this invention can be used include isotopes of iron, nickel, zinc and tin, with iron usually being preferred.

The metering system can also be arranged to count the number of metal particles per unit time in the flowing fluid in the pipe. If the fluid is a coal-derived liquid containing ash having a known metal content, the meter system and method can also be used to determine the ash concentration of the flowing liquid, for which a correlation between the metal particles and the ash concentration of the coal-derived liquid is known.

DETAILED DESCRIPTION OF INVENTION

Figure 1:
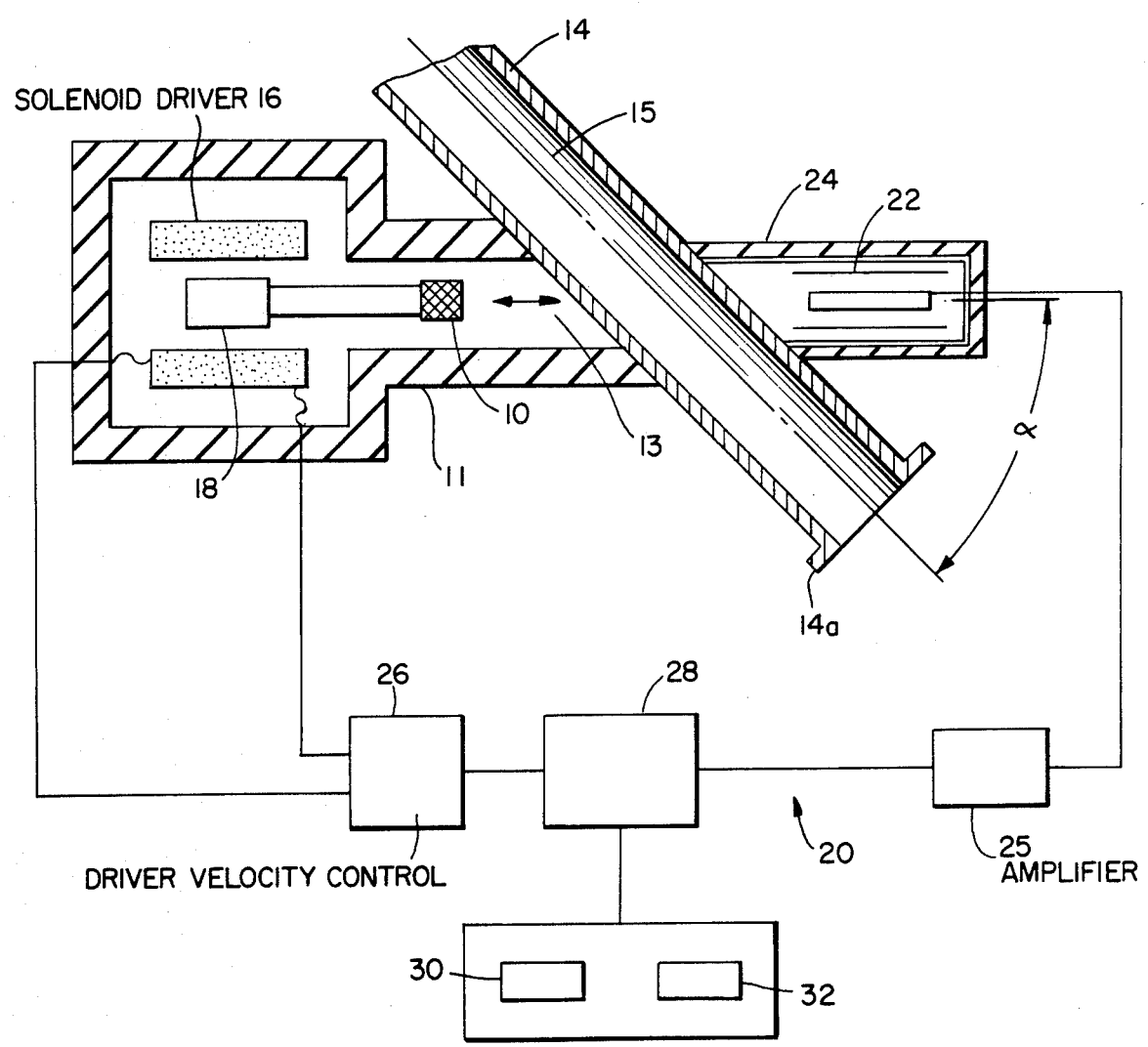
FIG. 1 is a schematic view showing the fluid flow and ash concentration metering system and method of the present invention.

A flow metering system as generally shown in FIG. 1 is used to provide a continuous measurement of the velocity of a flowing fluid, such as a coal-derived liquid flowing in a pipe. A radioactive metal isotope source 10 such as cobalt-57 or iron is electrically shielded by material 11 except of opening 12, which is oriented toward the axis of pipe portion 14 at an angle $\alpha$ of about 15°-80°. The source 10 is oscillated by a suitable reciprocating drive means 16, such as a velocity transducer device, in such a way that the maximum forward velocity of source 10 exceeds the maximum fluid flow velocity component parallel to the gamma ray beam expected in the flowing fluid in pip 14. The axis of movement of the radioactive source opening 12 should be aligned with that of the flowing fluid in pipe 14 and located within a distance of about 0.1-0.5 feet. The velocity of the radioactive source 10 is continually monitored by an accelerometer means 18 incorporated in the source 10, and by an integrating electrical circuit 20. The gamma rays from radioactive source 10 are focused on the center of pipe 14, so that the flow direction of the fluid is generally longitudinal and flow straightening vanes in the pipe are not usually needed.

The velocity signal from accelerometer means 18 for the oscillating gamma ray source 10 is fed to counter circuits along with a signal from gamma ray absorption detector 22 mounted on the opposite side of pipe portion 14 and radioactively shielded at 24 from the radioactive source 10. When the linear forward velocity of the source 10 substantially matches the velocity of the flowing fluid in pipe 14, the gamma rays emitted from source 10 will be absorbed by an isotope in iron particles 15 in the flowing fluid and such adsorption will be detected by proportional counter 22. A useful proportional counter 22 can contain a mixture of krypton and carbon dioxide gases. The signal from the gamma ray detector 22 can be used to latch a counter 28 which is monitoring the velocity of source 10, and display the velocity measured at the instant of absorption on a meter 30, thereby indicating the velocity of the flowing fluid in the pipe. If the material of pipe 14 contains a known concentration of iron, the electrical circuitry can be designed so as to exclude such fixed amounts of iron from the meter reading. Alternatively, the portion 14a of the pipe in the gamma ray detector zone, i.e., the pipe portion surrounded by detector 22, can be made of a non-ferrous material such as aluminum beryllium or copper. A description of Mossbauer components and circuitry can be found in "An Introduction to Mossbauer Spectroscopy", by L. May, Chapters 1 and 2, Plenum Press, 1981, which is incorporated herein by reference.

The range of fluid velocities for which the flow meter of this invention is useful is limited only by the components of the angle between the movement axis of the radioactive source and the centerline of the pipe, and the practical acceleration limit for the gamma ray source 10, and usually does not exceed about 30 ft/sec and is preferably 2-25 ft/sec. The flowing fluid for which velocity is measured can also contain gamma ray absorbing isotopes of other elements such as nickel, zinc, and tin used for measuring the flowing velocity of fluids containing these elements, but iron is usually preferred because of convenience of use.

The absorption detector 22 can also be used to detect the number of gamma ray absorbing particles in pipe 14 per unit time. The counter 28 can display on meter 32 the number of particle counts from which the detector 22, which is related to the metal (iron) content of the flowing fluid. For coal-derived liquids containing ash of a known iron composition, this meter 32 indicates the ash content of the flowing liquid. Oscillating radioactive sources containing different radioactive elements could also be used to monitor the concentration of different elements in the flowing coal liquid, such as nickel, zinc and tin.

This metering system can be used for a wide range of flowing fluid temperatures, which is limited only by the gamma ray absorption of the metal isotopes in the flowing fluid and the material of pipe 14. Useful fluid temperatures are within a range of about 50°–1000° F. The pressure of the flowing fluid is limited only by the thickness of the pipe wall, which can be up to a practical limit of about 0.6 inches thick, and taken together with a pipe inside diameter up to about 2 inches and the allowable stress for the material will determine the working pressure rating of the pipe.

Although this invention has been described broadly and with reference to certain preferred embodiments thereof, it will be understood that modifications and variations of the flow meter system and method for use can be made within the spirit and scope of the invention, which is defined by the following claims.

I claim:

1. A flow meter system for measuring the velocity of a flowing fluid, comprising:
   (a) a pipe through which said fluid flows, said fluid containing a gamma ray absorbing metal isotope;
   (b) a radioactive source of gamma rays positioned adjacent to said pipe, said source of radiation being oriented toward the pipe and oscillated in a direction at an angle of about 15° to about 80° to the fluid flowing in said pipe;
   (c) a gamma ray detector means positioned adjacent to said pipe on a side opposite said radioactive source for detecting the presence of said metal isotope contained in the flowing fluid; and
   (d) electrical means for monitoring the velocity of said oscillating gamma ray source and the metal particles in the fluid flowing in said pipe, and thereby measure the velocity of the following fluid.

2. The flow meter system of claim 1, wherein the velocity of said gamma ray source is monitored by an acceleration device incorporated therein.

3. The flow meter system of claim 1, wherein said gamma ray detection means is a proportional counter radioactively shielded from said gamma ray source.

4. The flow meter system of claim 1, wherein said oscillating motion of the gamma ray source is provided electrically by a velocity transducer device.

5. The flow meter system of claim 1, wherein said flowing fluid is a coal-derived liquid containing iron compounds, said source is cobalt-57 and the absorbing metal in the coal slurry is iron.

6. The flow meter system of claim 1, wherein the pipe through which the gamma rays pass comprises a non-ferrous material.

7. The flow meter system of claim 5, wherein a counter means is provided to detect and measure the concentration of absorbing metal in said flowing liquid so as to determine the ash concentration of the flowing liquid.

8. The flow meter system for measuring the velocity of a flowing fluid, comprising:
   (a) a pipe through which said fluid flows, said fluid containing a gamma ray absorbing metal isotope;
   (b) a radioactive source of gamma rays positioned adjacent to said pipe, said source of radiation being oriented toward the pipe and electromagnetically oscillating in a direction at angle of about 15° to about 80° to the fluid flowing in said pipe;
   (c) a gamma ray detector means positioned adjacent said pipe on a side opposite said radioactive source for detecting the presence of said metal isotope contained in the flowing fluid; and
   (d) electrical circuit means for monitoring the velocity of said oscillating gamma ray source, and the metal particles in the flowing fluid in said pipe, and thereby measuring the velocity of the flowing fluid in the pipe, and displaying the velocity of the flowing fluid in said pipe.

9. A method for measuring velocity of a flowing fluid containing a metal isotope within a pipe; comprising:
   (a) flowing a fluid containing a gamma ray absorbing metal isotope at temperature of 50°–1000° F. through a pipe;
   (b) moving a gamma ray radiation source aligned with said pipe portion in reciprocating motion in a direction angled at 15°–90° to said pipe and at a forward velocity at least equal that of the flowing fluid and not exceeding about 30 ft/sec, and causing the metal isotope in said flowing fluid to partially absorb said gamma rays;
   (c) monitoring the forward velocity of said gamma ray radiation source using an accelerometer means;
   (d) monitoring the flowing fluid in said pipe portion with gamma ray detection means to detect the presence of metal isotope containing particles in the flowing fluid; and (e) determining from said accelerometer the forward velocity of said radiation source at the time when the metal particles in the flowing fluid are absorbing gamma rays, said velocity of the radiation source being substantially the same velocity as the flowing fluid in the pipe portion.

10. A method for measuring velocity of a flowing fluid containing a metal isotope within a pipe, comprising:
   (a) flowing a fluid containing a gamma ray absorbing metal isotope through a pipe;
   (b) moving a gamma ray radiation source aligned with said pipe in reciprocating motion in a direction angled to said pipe at a forward velocity at least equal to that of the flowing fluid, and causing the metal isotope in said flowing fluid to partially absorb said gamma rays;
   (c) monitoring the forward velocity of said gamma ray radiation source using accelerometer means;
   (d) monitoring the flowing fluid in said pipe portion with gamma ray detection means to detect the presence of metal isotope containing particles in the flowing fluid; and
   (e) determining from said accelerometer the forward velocity of said radiation source at the time when the metal particles in the flowing fluid are absorbing gamma rays, said velocity of the radiation source being substantially the same velocity as the flowing fluid in the pipe portion.

11. The method of claim 10, wherein said flowing fluid is a coal-derived liquid.

12. The method of claim 11, wherein the maximum forward linear velocity of said radiation source exceeds the velocity of the flowing fluid.

13. The method of claim 11, wherein the velocity of said flowing fluid does not exceed about 3 ft/sec.

14. The method of claim 11, wherein the temperatures of said flowing fluid is 50°–1000° F.

15. The method of claim 11, wherein the metal isotope in the flowing fluid are iron compounds.

* * * * *